(12) United States Patent
Masumoto et al.

(10) Patent No.: US 8,913,713 B2
(45) Date of Patent: Dec. 16, 2014

(54) RADIOGRAPHIC IMAGE GENERATION DEVICE AND METHOD

(71) Applicant: FUJIFILM Corporation, Tokyo (JP)

(72) Inventors: Jun Masumoto, Ashigarakami-gun (JP); Masahiko Yamada, Ashigarakami-gun (JP); Hiroaki Yasuda, Ashigarakami-gun (JP); Yasuko Yahiro, Ashigarakami-gun (JP); Nobuhiko Kashiwagi, Ashigarakami-gun (JP); Ayako Muramoto, Ashigarakami-gun (JP); Haruyasu Nakatsugawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/020,681

(22) Filed: Sep. 6, 2013

(65) Prior Publication Data

US 2014/0093029 A1 Apr. 3, 2014

(30) Foreign Application Priority Data

Sep. 28, 2012 (JP) .................................. 2012-216129

(51) Int. Cl.
*G01N 23/00* (2006.01)
*G06K 9/00* (2006.01)
*A61B 6/00* (2006.01)
*A61B 6/02* (2006.01)

(52) U.S. Cl.
CPC .................. *A61B 6/502* (2013.01); *A61B 6/025* (2013.01)
USPC ............................................ 378/21; 382/131

(58) Field of Classification Search
CPC ........ A61B 6/032; A61B 6/025; A61B 6/502; A61B 6/022; A61B 6/505; G01N 23/04
USPC ......... 378/4, 21–27, 37, 41, 54, 62, 204, 210, 378/901; 382/128, 131, 166, 232–234, 244, 382/325
See application file for complete search history.

(56) References Cited

U.S. PATENT DOCUMENTS

2006/0029268 A1\* 2/2006 Endo et al. .................... 382/132
2008/0247509 A1 10/2008 Kashiwagi

FOREIGN PATENT DOCUMENTS

JP H 6-189952 7/1994

\* cited by examiner

*Primary Examiner* — Hoon Song
*Assistant Examiner* — Mona M Sanei
(74) *Attorney, Agent, or Firm* — McGinn IP Law Group, PLLC

(57) ABSTRACT

Radiographic images for different imaging directions taken by applying radiation to a subject from the different imaging directions are obtained, and a plurality of first tomographic images having a first slice thickness are generated based on the obtained plurality of radiographic images and a plurality of second tomographic images having a second slice thickness that is greater than the first slice thickness are generated based on the radiographic images. Then, MinIP processing is applied to the first tomographic images to generate a MinIP image, and MIP processing is applied to the second tomographic images to generate a MIP image. Then, combining processing is performed using the MinIP image and the MIP image to generate a composite image.

12 Claims, 8 Drawing Sheets

RADIOGRAPHIC IMAGE GENERATION DEVICE AND METHOD

BACKGROUND OF THE INVENTION

1. Field of the Invention

The present invention relates to a radiographic image generation device and a radiographic image generation method wherein a plurality of tomographic images of a subject are generated based on a plurality of radiographic images obtained by applying radiation to the subject from different imaging directions, and a MinIP image and a MIP image are generated based on the tomographic images.

2. Description of the Related Art

In recent years, in order to observe an affected part of the body in more detail using a radiographic imaging apparatus, tomosynthesis imaging is proposed, where imaging operations are performed with applying radiation to the subject from different imaging directions by moving the radiation source to obtain a plurality of radiographic images, and the radiographic images are added to provide an image in which a desired slice plane is emphasized (see, for example, U.S. Patent Application Publication No. 20080247509).

In the tomosynthesis imaging, radiographic images of the subject, which are taken at different exposure angles with moving the radiation source parallel to the radiographic image detector or along a circular or elliptical trajectory depending on the characteristics of the imaging apparatus and necessary tomographic images, are obtained, and the radiographic images are reconstructed to generate tomographic images.

SUMMARY OF THE INVENTION

It is proposed to develop the above-described tomosynthesis imaging to the mammography. However, in the tomosynthesis imaging, a reduced radiation dose is used to take one radiographic image in order to minimize the exposure dose of the patient. This makes it difficult to observe a tumor mass, which relies on the optical density contrast. Further, since the mammographic imaging is performed in a state where the breast is compressed, it is difficult to obtain a sufficient resolution in the depth direction, and using tomographic images obtained by the mammographic imaging directly for volume rendering display does not always improve the diagnosis accuracy. Therefore, some device is necessary to display the tomographic images obtained by the mammographic imaging as a three-dimensional image.

More specifically, in the case where the tomosynthesis imaging is applied to the mammography, main objects to be observed by the doctor include calcified areas, which are formed by small isolated points, and a tumor area, which involves the mammary gland. In order to facilitate recognition of the three-dimensional structure of the tumor mass area, one may consider increasing the thickness of a tomographic image, thereby providing higher optical density contrast of the displayed image. In this case, however, the calcified areas formed by isolated points, which are many and scattered three-dimensionally, are highly likely to disappear or be difficult to see when the thickness of the tomographic image is increased.

Japanese Unexamined Patent Publication No. 6 (1994)-189952 discloses displaying an image formed by adding a MIP image and a MinIP image; however, it discloses nothing about a method for clearly displaying both the calcified areas and the tumor mass area, as described above.

In view of the above-described circumstances, the present invention is directed to providing a radiographic image generation device and a radiographic image generation method which allow displaying both the calcified areas and the tumor mass area, as described above, with high resolution in the depth direction, thereby improving the diagnosis accuracy.

An aspect of the radiographic image generation device of the invention is a radiographic image generation device for generating tomographic images based on radiographic images for different imaging directions taken by applying radiation to a subject from the different imaging directions, the device including: a radiographic image obtaining unit for obtaining the radiographic images for the different imaging directions; a tomographic image generation unit for generating a plurality of first tomographic images having a first slice thickness based on the plurality of radiographic images obtained by the radiographic image obtaining unit and generating a plurality of second tomographic images having a second slice thickness that is greater than the first slice thickness based on the radiographic images; a MinIP processing unit for applying MinIP processing to the first tomographic images to generate a MinIP image; a MIP processing unit for applying MIP processing to the second tomographic images to generate a MIP image; and a composite image generation unit for performing combining processing using the MinIP image and the MIP image to generate a composite image.

The radiographic image generation device of the invention may further include a high frequency extraction processing unit for applying high frequency extraction processing to extract high-frequency components to the MinIP image, wherein the composite image generation unit generates the composite image using the MinIP image subjected to the high-frequency extraction processing.

The radiographic image generation device of the invention may further include a high frequency suppression processing unit for applying high-frequency suppression processing to suppress high-frequency components to the MIP image, wherein the composite image generation unit generates the composite image using the MIP image subjected to the high-frequency suppression processing.

The tomographic image generation unit may set the first slice thickness or the second slice thickness based on at least one of a range of the imaging directions of the radiographic images used to generate the first and second tomographic images, a type of a radiation source for applying the radiation, a thickness of the subject and patient information of the subject.

The radiographic image generation device of the invention may further include a display control unit for displaying the composite image.

The display control unit may display the MinIP image and the MIP image in the composite image in different colors.

The display control unit may display the radiographic image, the first tomographic image or the second tomographic image side by side with the composite image.

The radiographic image generation device of the invention may further include a volume-rendered image generation unit for generating a volume-rendered image using a plurality of tomographic images that are generated based on the radiographic images, wherein the display control unit displays the volume-rendered image side by side with the composite image.

The radiographic image generation device of the invention may further include: a volume-rendered image generation unit for generating a volume-rendered image using a plurality of tomographic images that are generated based on the radiographic images; and an image selection receiving unit for receiving a selection of an image to be displayed from the radiographic images, the first tomographic images, the second tomographic images and the volume-rendered image, wherein the display control unit displays the image to be displayed received by the image selection receiving unit.

The high-frequency component extraction processing may use high-pass filtering.

The high-frequency suppression processing may user low-pass filtering.

An aspect of the radiographic image generation method of the invention is a radiographic image generation method for generating tomographic images based on radiographic images for different imaging directions taken by applying radiation to a subject from the different imaging directions, the method including: obtaining the radiographic images for the different imaging directions; generating a plurality of first tomographic images having a first slice thickness based on the obtained plurality of radiographic images and generating a plurality of second tomographic images having a second slice thickness that is greater than the first slice thickness based on the radiographic images; applying MinIP processing to the first tomographic images to generate a MinIP image; applying MIP processing to the second tomographic images to generate a MIP image; and performing combining processing using the MinIP image and the MIP image to generate a composite image.

According to the radiographic image generation device and method of the invention, radiographic images for different imaging directions taken by applying radiation to a subject from the different imaging directions are obtained, and a plurality of first tomographic images having a first slice thickness are generated based on the obtained plurality of radiographic images and a plurality of second tomographic images having a second slice thickness that is greater than the first slice thickness are generated based on the radiographic images. Then, MinIP processing is applied to the first tomographic images to generate a MinIP image, and MIP processing is applied to the second tomographic images to generate a MIP image. Then, combining processing is performed using the MinIP image and the MIP image to generate a composite image. This allows clearly showing calcified areas in the MinIP image based on the tomographic images having the relatively small slice thickness, and clearly showing the three-dimensional structure of a tumor mass area in the MIP image with high optical density contrast based on the tomographic images having the relatively large slice thickness. Therefore, both the calcified areas and the tumor mass area can be displayed with high resolution in the depth-direction, thereby improving the diagnosis accuracy.

Further, in the case where the radiographic image generation device of the invention is configured to apply the high-frequency extraction processing to extract high-frequency components to the MinIP image, calcified areas can be shown more clearly. In the case where the radiographic image generation device of the invention is configured to apply the high-frequency suppression processing to suppress high-frequency components to the MIP image, the three-dimensional structure of a tumor mass area can be shown more clearly.

Further, in the case where the radiographic image generation device of the invention is configured to set the first slice thickness or the second slice thickness based on at least one of the range of the imaging directions of the radiographic images used to generate the first and second tomographic images, the type of a radiation source for applying the radiation, the thickness of the subject and patient information of the subject, the slice thickness can be set with taking not only the size and the shape of the calcified areas and the tumor mass area but also various other conditions into account, and this allows generating the first and second tomographic images more suitable for the imaging diagnosis.

Further, in the case where the MinIP image and the MIP image in the composite image are displayed in different colors, the calcified areas and the tumor mass area can be more clearly distinguished from one another.

Further, in the case where images to be displayed are arbitrarily selected from the radiographic images, the first and second tomographic images, the composite image and the volume-rendered image and are displayed side by side, desired images can be displayed side by side, as appropriate, to compare them with each other, thereby improving the imaging diagnosis and making the imaging diagnosis more efficient.

DESCRIPTION OF THE PREFERRED EMBODIMENTS

Figure 1:
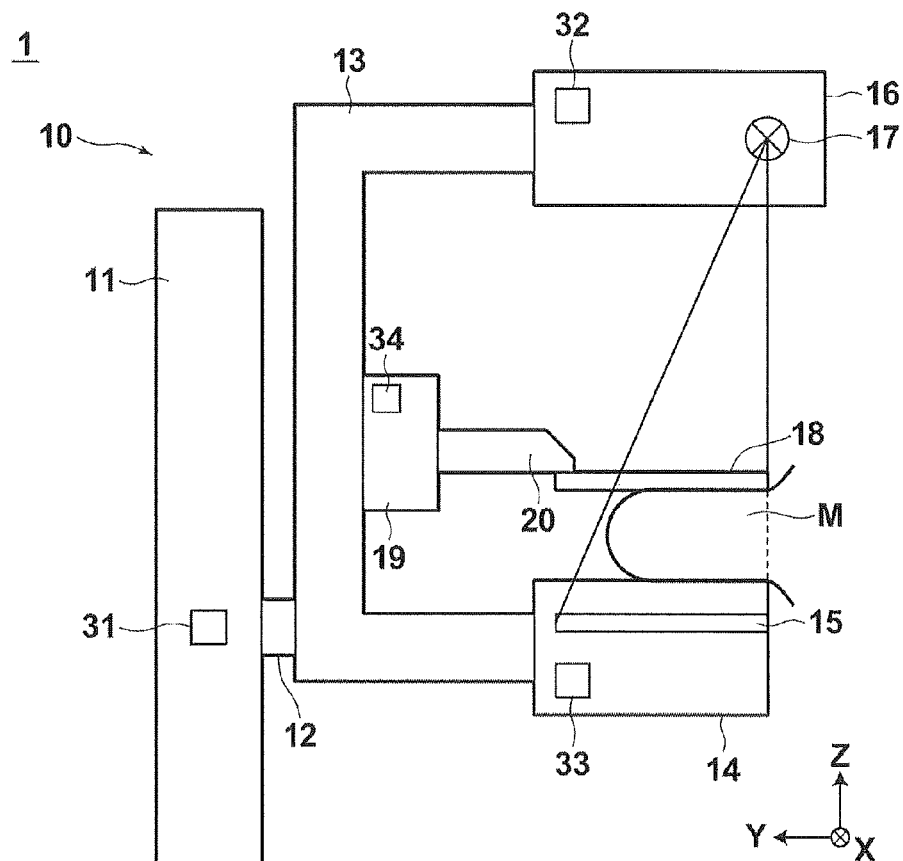
FIG. 1 is a diagram illustrating the schematic structure of a mammographic imaging and display system employing one embodiment of a radiographic image generation device of the present invention.
Figure 1:
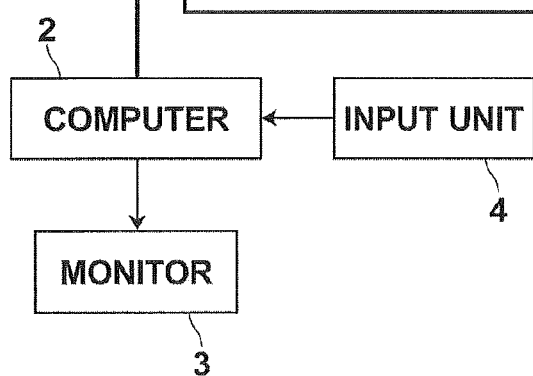

Now, a mammographic imaging and display system employing one embodiment of a radiographic image generation device and a radiographic image generation method of the present invention will be described with reference to the drawings. The mammographic imaging and display system of this embodiment has a tomosynthesis imaging function, and is configured to be capable of taking tomographic images of the breast. FIG. 1 is a diagram illustrating the schematic configuration of the entire mammographic imaging and display system of this embodiment.

As shown in FIG. 1, a mammographic imaging and display system 1 of this embodiment includes: a mammographic imaging apparatus 10 for obtaining radiographic images of a breast, which is the subject, for different imaging directions by applying radiation to the breast from the different imaging directions; a computer 2 for reconstructing the plurality of radiographic images obtained by the mammographic imaging apparatus 10 to generate a plurality of tomographic images, and generating a MIP image and a MinIP image based on the tomographic images; a monitor 3 for displaying the images generated by the computer 2; and an input unit 4 for receiving various settings inputted by the user.

Figure 2:
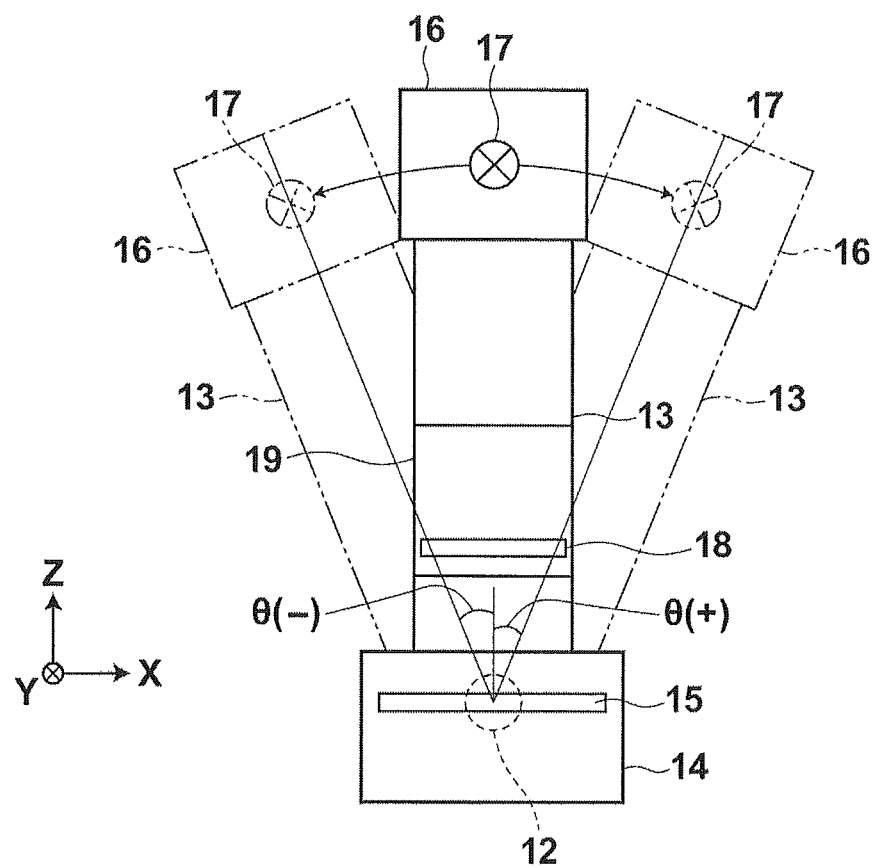
FIG. 2 is a diagram illustrating an arm of the mammographic imaging and display system shown in FIG. 1 viewed from the right side in FIG. 1.

As shown in FIG. 1, the mammographic imaging apparatus 10 includes a base 11, a rotation shaft 12 that is rotatable and is movable in the vertical direction (the Z-direction) relative to the base 11, and an arm 13 that is connected to the base 11 via the rotation shaft 12. FIG. 2 shows the arm 13 viewed from the right side of FIG. 1.

The arm 13 is C-shaped, and is provided with an imaging table 14 at one end thereof and a radiation exposure unit 16 at the other end thereof such that the radiation exposure unit 16 faces the imaging table 14. The rotation and the movement in the vertical direction of the arm 13 are controlled by an arm controller 31, which is built in the base 11.

The imaging table 14 contains therein a radiographic image detector 15, such as a flat panel detector, and a detector controller 33, which controls reading of electric charge signals from the radiographic image detector 15, etc.

The imaging table 14 also contains therein a circuit board, etc. The circuit board includes a charge amplifier for converting the electric charge signals read out from the radiographic image detector 15 into voltage signals, a correlated double sampling circuit for sampling the voltage signals outputted from the charge amplifier, an AD converter for converting the voltage signals into digital signals, etc.

As shown in FIG. 2, the imaging table 14 is attached to the arm 13 in such a positional relationship that the center of the radiographic image detector 15 is located on an extended line of the rotating shaft 12. The imaging table 14 is rotatably attached to the arm 13, and the orientation of the imaging table 14 can be fixed relative to the base 11 even when the arm 13 is rotated relative to the base 11.

The radiographic image detector 15 is of a type that is repeatedly usable to record and read a radiographic image. The radiation detector 15 may be a so-called direct-type radiographic image detector, which directly receives the radiation and generates electric charges, or may be a so-called indirect-type radiographic image detector, which once converts the radiation into visible light, and then converts the visible light into electric charge signals. As the reading system to read out the radiographic image signal, a so-called TFT reading system, which reads out the radiographic image signal with turning on and off TFT (thin film transistor) switches, or a so-called optical reading system, which reads out the radiographic image signal by applying reading light, may be used. As the indirect-type radiographic image detector, one using a CMOS (Complementary Metal Oxide Semiconductor) sensor or a CCD (Charge Coupled Device Image Sensor) may be used.

The radiation exposure unit 16 contains therein a radiation source 17 and a radiation source controller 32. The radiation source 17 may, for example, be one using Mo as a target and a filter material or one using Rh as a target and a filter material. Further, these radiation sources may be replaceable with one another.

The radiation source controller 32 controls timing of application of radiation from the radiation source 17, and radiation generation conditions (such as tube current, time, tube voltage, etc.) at the radiation source 17.

Further, a compression paddle 18 disposed above the imaging table 14 for holding and compressing the breast, a support 20 for supporting the compression paddle 18, and a moving mechanism 19 for moving the support 20 in the vertical direction (the Z-direction) are disposed at the middle portion of the arm 13. The position and the compressing pressure of the compression paddle 18 are controlled by a compression paddle controller 34.

Figure 3:
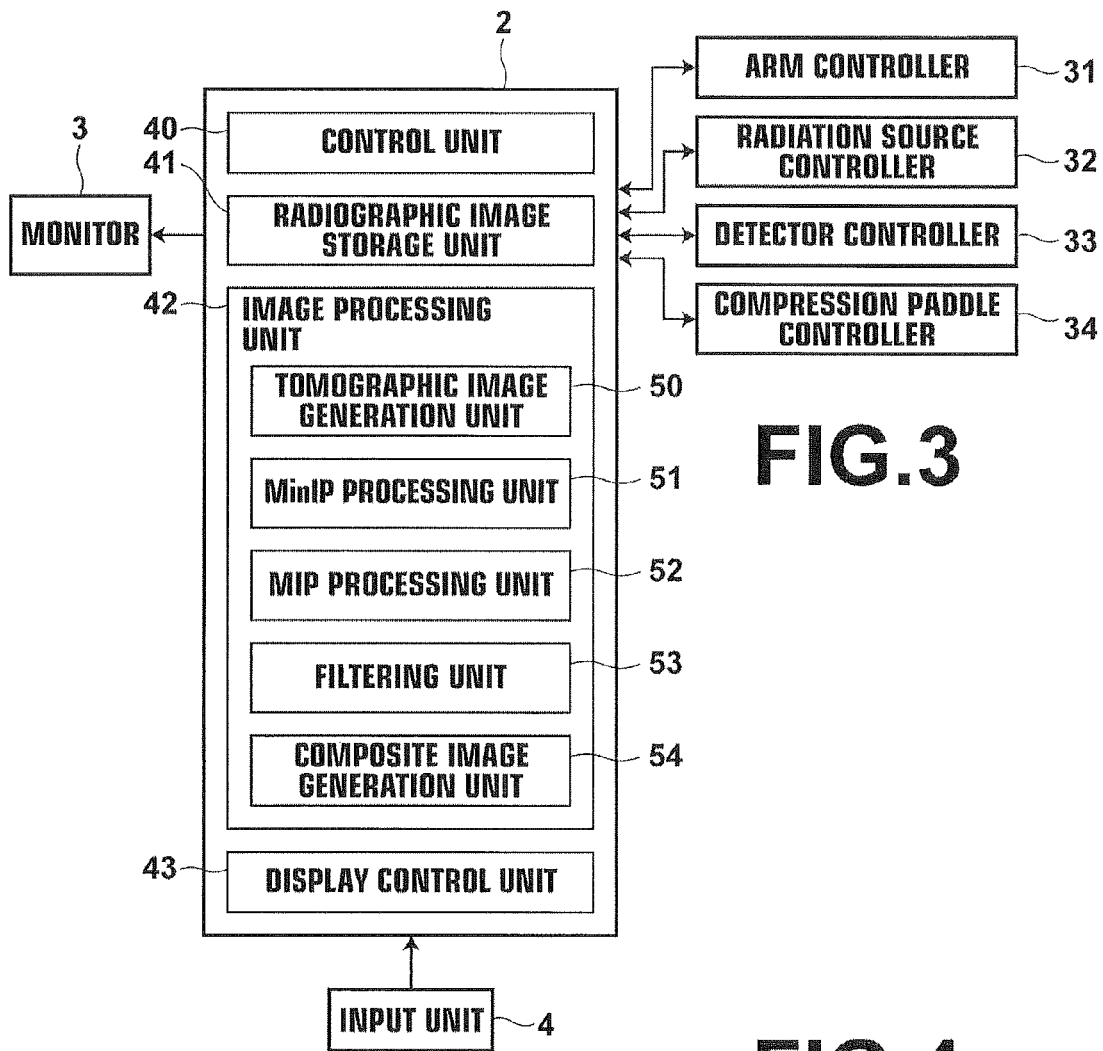
FIG. 3 is a block diagram illustrating the schematic internal structure of a computer of the mammographic imaging and display system shown in FIG. 1.

The computer 2 includes a central processing unit (CPU) and a storage device, such as a semiconductor memory, a hard disk, etc., and these hardware devices form a control unit 40, a radiographic image storage unit 41, an image processing unit 42 and a display control unit 43, as shown in FIG. 3.

The control unit 40 outputs predetermined control signals to the controllers 31 to 34 to control the entire system. A specific control method will be described in detail later.

The radiographic image storage unit 41 obtains and stores a plurality of radiographic images detected by the radiographic image detector 15 in the imaging operations of the breast M from different imaging directions. It should be noted that, in this embodiment, the radiographic image storage unit 41 corresponds to a radiographic image obtaining unit recited in the claims.

The image processing unit 42 includes a tomographic image generation unit 50, a MinIP processing unit 51, a MIP processing unit 52, a filtering unit 53, and a composite image generation unit 54.

The tomographic image generation unit 50 reads out the radiographic images stored in the radiographic image storage unit 41, and generates a plurality of first tomographic images having a first slice thickness using the radiographic images, and also generates a plurality of second tomographic images having a second slice thickness, which is greater than the first slice thickness, using the radiographic images.

In this embodiment, the first slice thickness of the first tomographic images and the second slice thickness of the second tomographic image described above are set based on the range of imaging directions of the radiographic images used to generate the tomographic images (i.e., the angle of the arc of the trajectory of the radiation source 17), the type of the radiation source 17, the thickness of the compressed breast M and patient information. The reason for setting the slice thicknesses based on these conditions is as follows.

First, the reason for determining the slice thicknesses depending on the range of imaging directions of the radiographic images used to generate the tomographic images (i.e., the angle of the arc of the trajectory of the radiation source 17) is that a larger range of imaging directions makes it more likely that calcifications and a tumor mass in the breast are projected on the radiographic images without overlapping one another, thereby allowing clearly observing them even when small slice thicknesses are set. Further, a larger range of imaging directions results in lower sharpness and resolution of the radiographic images, and therefore it is desirable to set smaller slice thicknesses for a larger range of imaging directions.

Therefore, in this embodiment, smaller first and second slice thicknesses are set for a larger range of imaging directions.

The reason of the lower sharpness and resolution for a larger range of imaging directions is that a larger range of imaging directions, i.e., a greater inclination of the imaging direction from the direction perpendicular to the radiographic image detector 15 means a greater inclination of the incident angle of radiation passing through a given point in the breast and entering the detection surface of the radiographic image detector 15. Then, an electric charge signal generated by the radiation entering the detection surface at such an inclined direction is detected across a plurality of pixels (a plurality detection elements) rather than at one pixel (one detection element).

Next, the reason for setting the slice thicknesses depending on the type of the radiation source 17 is as follows. Examples of the type of the radiation source 17 used in mammography include one using Mo as a target and a filter material (which will hereinafter be referred to as "Mo/Mo radiation source"), and one using Rh as a target and a filter material (which will hereinafter be referred to as "Rh/Rh radiation source").

Figure 4:
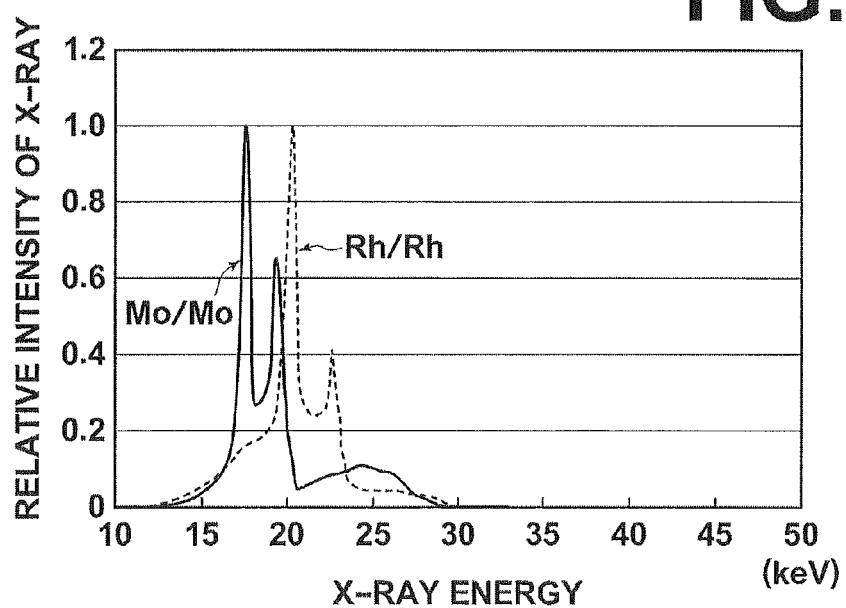
FIG. 4 is a diagram showing characteristics of radiation sources.

As shown in FIG. 4, the Mo/Mo radiation source has characteristic X-rays at 17 KeV and 20 KeV and a K absorption edge at 20 KeV, and the Rh/Rh radiation source has characteristic X-rays at 20 KeV and 23 KeV and a K absorption edge at 23 KeV.

It is said that, in general, an X-ray energy exceeding 20 KeV is a factor causing low image quality (low contrast), rather than used for imaging.

That is, under the condition where the thickness of the breast M is the same, for example, the contrast is lower in the case where the Rh/Rh radiation source is used than in the case where the Mo/Mo radiation source is used.

Since the observation of a tumor mass relies on the optical density contrast, it is difficult to observe a tumor mass on a low-contrast image.

Therefore, with respect to the second slice thickness of the second tomographic images forming a MIP image, which is mainly used to observe a tumor mass, as described later, a greater slice thickness is set in the case where the Rh/Rh radiation source is used than that in the case where the Mo/Mo radiation source is used. This allows obtaining an image with sufficient contrast even when the Rh/Rh radiation source is used.

Next, the reason for determining the slice thicknesses depending on the thickness of the compressed breast is as follows. A larger thickness of the compressed breast means a larger X-ray absorption in the breast M, and influence of the X-ray absorption difference in the depth direction is also increased. Therefore, an excessively large slice thickness leads to low diagnosis accuracy.

Therefore, in this embodiment, smaller first and second slice thicknesses are set for a larger thickness of the compressed breast.

Next, the reason for determining the slice thicknesses based on the patient information is as follows. The patient information includes information about the presence or absence of mastopathy. Then, if the patient has mastopathy, for example, it is important that how well the tumor mass is extracted since X-ray absorption coefficients of the tumor mass and the mammary gland are almost the same. Therefore, in the case where the patient has mastopathy, the second slice thickness of the second tomographic images forming the MIP image used to observe the tumor mass is set to be greater than that in the case where the patient does not have mastopathy. It should be noted that the first slice thickness of the first tomographic images forming the MinIP image used to observe the calcifications may not be changed depending on the presence or absence of mastopathy. However, in order to facilitate observation of dot-like calcifications, it is desirable to set a smaller slice thickness in the case where the patient has mastopathy than that in the case where the patient does not have mastopathy.

The patient information also includes information of the age of the patient. If the patient is young, the mammary gland of the patient is generally developed. Therefore, similarly to the above-described case of mastopathy, a large slice thickness is set as the second slice thickness of the second tomographic images forming the MIP image used to observe a tumor mass. In contrast, if the patient is old, the mammary gland is less developed. Therefore, a smaller slice thickness is set as the second slice thickness than that in the case where the patient is young. It should be noted that, when a smaller slice thickness is set as the second slice thickness, the number of the second tomographic images is increased accordingly, resulting in a longer time taken for image interpretation of the second tomographic images. Therefore, the second slice thickness may not be changed from a typical slice thickness even in the case where the patient is old, for example, if no problem, such as re-examination, is found in the history of diagnosis results included in the patient information.

For the reasons as described above, the tomographic image generation unit 50 sets the first slice thickness and the second slice thickness based on the range of imaging directions (i.e., the angle of the arc of the trajectory of the radiation source 17), the type of the radiation source 17, the thickness of the compressed breast and the patient information. In the tomographic image generation unit 50, a table containing values of the first and second slice thicknesses corresponding to the above-described various conditions is set in advance, so that the tomographic image generation unit 50 sets the first and second slice thicknesses based on the various conditions inputted thereto. It should be noted that the range of imaging directions, the type of the radiation source 17 and the patient information are inputted by the user via the input unit 4, for example. The thickness of the compressed breast is calculated by the compression paddle controller 34 based on positional information of the compression paddle 18, and the calculated thickness of the breast M is inputted to the tomographic image generation unit 50.

Next, examples of the first and second slice thicknesses to be set based on the above-described various conditions are described.

First, based on the shape conditions where calcifications are relatively small and about 5 mm in size and a tumor mass is relatively large and is about 10 mm in size, a typical first slice thickness of 5 mm and a typical second slice thickness of 10 mm are set, and these thicknesses are changed based on the above-described various conditions to set the first and second slice thicknesses depending on the conditions.

Specifically, in the case where the range of imaging directions is 10° (±5°), the type of the radiation source 17 is the Mo/Mo radiation source and the thickness of the breast M is 40 mm, for example, the first and second slice thicknesses are set to be typical slice thicknesses, namely, the first slice thickness is set to be 5 mm and the second slice thickness is set to be 10 mm.

On the other hand, in the case where the range of imaging directions is changed to be 20° (±10°) and the type of the radiation source 17 and the thickness of the breast M are the same, the first and second slice thicknesses are set to be smaller than the typical first and second slice thicknesses, such that the first slice thickness is set to be 4 mm and the second slice thickness is set to be 8 mm. It should be noted that, in the case where the range of imaging directions is 20° (±10°), the second slice thickness of 8 mm, as described above, may results in degraded images. Therefore, for example, the second slice thickness may be set to be 6 mm, and the value of a threshold value Thmax used in MIP processing, which will be described later, may be set to be smaller than the value set under the typical conditions.

Further, in the case where the thickness of the breast M is changed to be 80 mm from the conditions under which the above-described typical first and second slice thicknesses are set, and the type of the radiation source 17 and the range of imaging directions are the same, the first and second slice thicknesses are set to be smaller than the typical first and second slice thicknesses, such that the first slice thickness is set to be 3 mm and the second slice thickness is et to be 6 mm.

Further, in the case where the type of the radiation source 17 is changed to be the Rh/Rh radiation source from the conditions under which the above-described typical first and second slice thicknesses are set, and the range of imaging directions and the thickness of the breast M are the same, only the second slice thickness is set to be greater than the typical second slice thickness, such that the first slice thickness is set to be 5 mm and the second slice thickness is set to be 12 mm.

Further, in the case where the information of mastopathy is added as the patient information to the conditions under which the above-described typical first and second slice thicknesses are set, and the type of the radiation source 17, the range of imaging directions and the thickness of the breast M are the same, only the second slice thickness is set to be greater than the typical second slice thickness, such that the first slice thickness is set to be 5 mm and the second slice thickness is set to be 12 mm. However, in view of the extraction of dot-like calcifications, as described above, it is desirable to set the first slice thickness to be 4 mm.

Further, in the case where information indicating that the patient is in her twenties is added as the patient information to the conditions under which the above-described typical first and second slice thicknesses are set, and the type of the radiation source 17, the range of imaging directions and the thickness of the breast M are the same, only the second slice thickness is set to be greater than the typical second slice thickness, such that the first slice thickness is set to be 5 mm and the second slice thickness is set to be 12 mm.

Further, in the case where information indicating that the patient is in her seventies is added as the patient information to the conditions under which the above-described typical first and second slice thicknesses are set, and the type of the radiation source 17, the range of imaging directions and the thickness of the breast M are the same, only the second slice thickness is set to be smaller than the typical second slice thickness, such that the first slice thickness is set to be 5 mm and the second slice thickness is set to be 8 mm.

The above is the explanation of the first and second slice thicknesses of the first and second tomographic images generated by the tomographic image generation unit 50.

Then, the MinIP processing unit 51 applies MinIP (Minimum Intensity Projection) processing to the first tomographic images generated by the tomographic image generation unit 50 to generate a MinIP image. The MinIP processing uses the minimum signal value in each line of sight as the signal value of the line of sight. The MinIP image generated by the MinIP processing unit 51 is suitable for observing mainly calcifications in the breast.

In the MinIP processing unit 51, a threshold value Thmin is set based on the first slice thickness of the first tomographic images. When the MinIP processing unit 51 performs the MinIP processing, signals not greater than the threshold value Thmin are determined not to be displayed and signals greater than the threshold value Thmin are determined to be displayed, and the minimum signal value among the signals greater than the threshold value Thmin in each line of sight is obtained. It should be noted that a greater value of the threshold value Thmin is set for a larger first slice thickness. The MinIP processing is a known technique and therefore the detailed description thereof is omitted.

The MIP processing unit 52 applies MIP (Maximum Intensity Projection) processing to the second tomographic images generated by the tomographic image generation unit 50 to generate a MIP image. The MIP processing uses the maximum signal value in each line of sight as the signal value of the line of sight. The MIP image generated by MIP processing unit 52 is suitable for observing mainly a tumor mass in the breast.

In the MIP processing unit 52, a threshold value Thmax is set based on the second slice thickness of the second tomographic images. When the MIP processing unit 52 performs the MIP processing, signals greater than the threshold value Thmax are determined not to be displayed and signals not greater than the threshold value Thmax are determined to be displayed, and the maximum signal value among the signals not greater than the threshold value Thmax in each line of sight is obtained. It should be noted that a greater value of the threshold value Thmax is set for a larger second slice thickness. The MIP processing is a known technique and therefore the detailed description thereof is omitted.

The filtering unit 53 applies different types of filtering to the MinIP image generated by the MinIP processing unit 51 and the MIP image generated by the MIP processing unit 52, respectively. In this embodiment, the filtering unit 53 corresponds to a high frequency extraction processing unit and a high frequency suppression processing unit recited in the claims.

Specifically, the filtering unit 53 in this embodiment applies processing to extract high-frequency components to the MinIP image. An example of this type of filtering is high-pass filtering; however, any other known filtering method may be used.

On the other hand, the filtering unit 53 in this embodiment applies processing to suppress high-frequency components to the MIP image. An example of this type of filtering is low-pass filtering; however, any other known filtering method may be used.

The composite image generation unit 54 generate a composite image by combining the MinIP image and the MIP image subjected to the filtering by the filtering unit 53.

The display control unit 43 applies predetermined processing to the radiographic image stored in the radiographic image storage unit 41, the first or second tomographic image generated by the tomographic image generation unit 50 and/or the composite image generated by the composite image generation unit 54 and displays the image(s) on the monitor 3.

It should be noted that, when a composite image is generated on the monitor 3, it is desirable to display the MinIP image and the MIP image in the composite image in different colors. The colors of the MinIP image and the MIP image may be arbitrarily set by the user via the input unit 4. At this time, a color template for setting the colors of the MinIP image and the MIP image may be displayed on the monitor 3.

The input unit 4 is formed by a pointing device, such as a keyboard and a mouse, and receives an input of various setting, such as the first and second slice thicknesses, the threshold value Thmin used in the MinIP processing and the threshold value Thmax used in the MIP processing, filtering conditions of the filtering applied to the MinIP image and the MIP image, etc. It should be noted that the filtering conditions may include, for example, cutoff frequencies for high-pass filtering and low-pass filtering.

Figure 5:
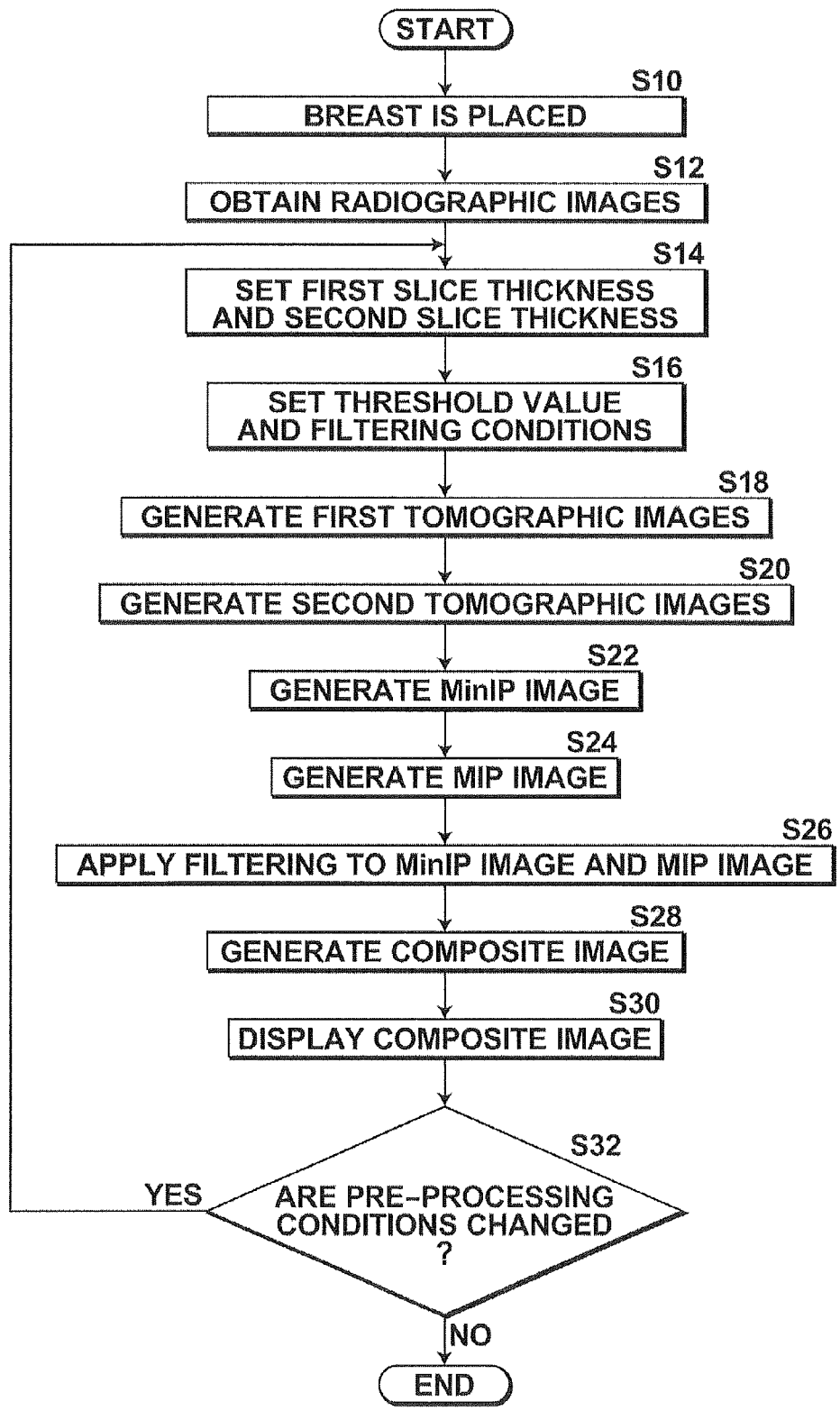
FIG. 5 is a flow chart for explaining operation of the mammographic imaging and display system employing one embodiment of the radiographic image generation device of the invention.

Next, operation of the mammographic imaging and display system 1 of this embodiment is described with reference to the flow chart shown in FIG. 5.

First, a breast M of the patient is placed on the imaging table 14, and the breast M is compressed by the compression paddle 18 at a predetermined pressure (S10).

Figure 6:
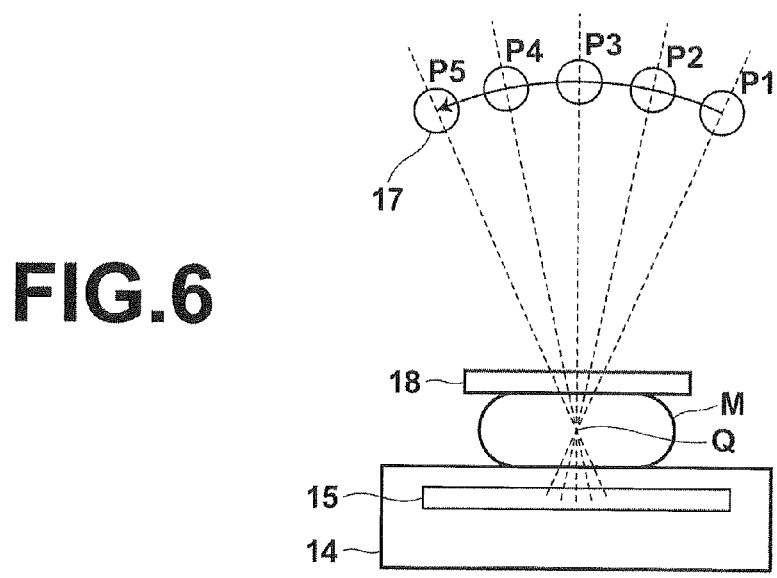
FIG. 6 is a diagram showing changes of the position of a radiation source of the mammographic imaging and display system shown in FIG. 1 from the start of imaging to the end of imaging, and a radiation exposure point Q.

Then, various imaging conditions are inputted by the user via the input unit 4, and an instruction to start imaging is inputted. When the instruction to start imaging is inputted, the arm controller 31 rotates the arm 13. FIG. 6 shows changes of the position of the radiation source 17 from the start of imaging to the end of imaging, and a radiation exposure point Q.

Specifically, first, the arm controller 31 rotates the arm 13 to bring the radiation source 17 into a position P1. In this embodiment, the position P1 corresponds to the imaging direction of +25°.

Then, the radiation source controller 32 controls the radiation source 17 so that the radiation is directed to the exposure point Q based on the radiation generation conditions of the radiation emitted from the position P1. It is preferred that the exposure point Q is a point about 2 cm above the center of the breast M placed on the top of the imaging table 14. Then, a radiographic image of the breast M is recorded as a latent charge image on the radiographic image detector 15.

Subsequently, the radiographic image recorded as the latent charge image on the radiographic image detector 15 is read out under control by the detector controller 33. The read out radiographic image is inputted to the computer 2 and stored in the radiographic image storage unit 41.

Then, the radiation source 17 is moved along an arcuate trajectory in the vicinity of the chest wall of the subject under control by the controllers, and a radiographic image of the breast is obtained for each position Pn (n=1 to 5 in the example shown in FIG. 6) along the trajectory and stored in the radiographic image storage unit 41 (S12).

It should be noted that, although only the five positions P1 to P5 are shown in FIG. 6 for the convenience of explanation, about ten to twenty radiographic images in the range of about ±25° relative to the direction perpendicular of the subject placement surface of the imaging table 14 (the detection surface of the radiographic image detector 15) are obtained in actual imaging operations, as mentioned above. The position P5 in this embodiment corresponds to an imaging direction of −25°.

Then, the first slice thickness for generating the first tomographic images and the second slice thickness for generating the second tomographic images at the tomographic image generation unit 50 are set (S14). Specifically, the range of imaging directions, the type of the radiation source 17 and the patient information are inputted by the user via the input unit 4, and the inputted conditions are inputted to the tomographic image generation unit 50. Also, the information of the thickness of the breast M calculated by the compression paddle controller 34 is inputted to the tomographic image generation unit 50. Then, at the tomographic image generation unit 50, the first slice thickness and the second slice thickness are set based on the conditions inputted thereto. It should be noted that, at this time, the information of the range of imaging directions set and inputted by the user is information within the range of ±25°, such as ±10° or ±20°. Then, when the tomographic images are generated by the tomographic image generation unit 50, the radiographic images taken from the imaging directions within the thus set and inputted range of imaging directions are used.

Subsequently, the threshold value Thmin used in the MinIP processing and the threshold value Thmax used in the MIP processing, as well as the filtering conditions of the filtering by the filtering unit 53 are set and inputted by the user via the input unit 4.

Then, the tomographic image generation unit 50 generates the first tomographic images having the first slice thickness and the second tomographic images having the second slice thickness (S18, S20).

Specifically, based on the range of imaging directions inputted to set the first and second slice thicknesses, the tomographic image generation unit 50 reads out the radiographic images in the range of imaging directions from the radiographic image storage unit 41, and generates tomographic images based on the radiographic images.

Figure 7:
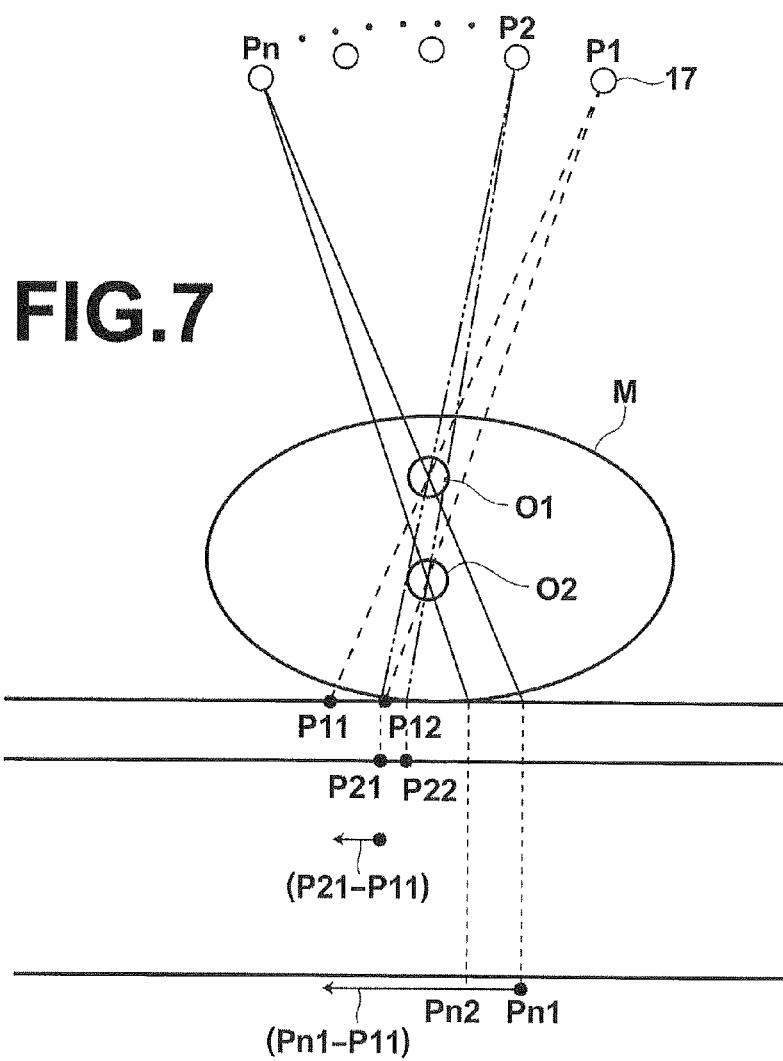
FIG. 7 is a diagram for explaining a method for generating a tomographic image based on a plurality of radiographic images.

Now, a method for generating a tomographic image in a case where the maximum range of)±25° (50° is inputted as the range of imaging directions, for example, is described. First, as shown in FIG. 7, the radiation source 17 is moved to each position P1, P2, . . . , and Pn, and radiation is applied to the breast M from each position to obtain radiographic images G1, G2, . . . , and Gn.

In a case where objects (O1, O2) present at different depths are projected from the position P1, for example, projection images of the objects appear at positions P11 and P12, respectively, on the radiographic image G1. When the objects (O1, O2) are projected from the position P2, projection images of the objects appear at positions P21 and P22, respectively, on the radiographic image G2. By repeating projection from the different radiation source positions P1, P2, . . . , and Pn in this manner, the object O1 is projected at positions P11, P21, . . . , and Pn1 and the object O2 is projected at positions P12, P22, . . . , and Pn2 correspondingly to the different radiation source positions.

Then, if it is wished to emphasize a slice plane where the object O1 is present, the radiographic image G2 is shifted by a distance of (P21-P11), the radiographic image G3 is shifted by a distance of (P31-P11), and the remaining radiographic image are shifted similarly to shift each taken image Gn by a distance of (Pn1-P11), and the thus shifted images are added to generate a tomographic image with a structure in the slice plane at the depth of the object O1 being emphasized.

If it is wished to emphasize a slice plane where the object O2 is present, the radiographic image G2 is shifted by a distance of (P22-P12), the radiographic image G3 is shifted by a distance of (P32-P12), and the remaining radiographic image are shifted similarly to shift each radiographic image Gn by a distance of (Pn2-P12), and the thus shifted images are added. By adding the radiographic images G1, G2, . . . , Gn with aligning the radiographic images depending on the position of the necessary slice in this manner, a tomographic image with a desired slice plane being emphasized can be obtained.

Then, in this embodiment, the first tomographic images having the first slice thickness and the second tomographic images having the second slice thickness are generated, as described above. Specifically, control of the slice thickness in a case where the slice thickness is 5 mm, for example, is achieved by adding five tomographic images having the slice thickness of 1 mm.

The first tomographic images generated by the tomographic image generation unit 50 are inputted to the MinIP processing unit 51. The MinIP processing unit 51 applies the MinIP processing to the first tomographic images inputted thereto to generate a MinIP image (S22).

The second tomographic images generated by the tomographic image generation unit 50 are inputted to the MIP processing unit 52. The MIP processing unit 52 applies the MIP processing to the second tomographic images inputted thereto to generate a MIP image (S24).

Then, the MinIP image generated by the MinIP processing unit 51 and the MIP image generated by the MIP processing unit 52 are inputted to the filtering unit 53. The filtering unit 53 applies the above-described filtering to each of the MinIP image and the MIP image inputted thereto (S26).

The MinIP image and the MIP image subjected to the filtering by the filtering unit 53 are inputted to the composite image generation unit 54. The composite image generation unit 54 combines the MinIP image and the MIP image subjected to the filtering and inputted thereto to generate a composite image (S28).

The composite image generated by the composite image generation unit 54 is outputted to the display control unit 43, and the display control unit 43 displays the composite image on the monitor 3 (S30).

If the user observing the composite image displayed on the monitor 3 wishes to change any of the pre-processing conditions, such as the first slice thickness, the second slice thickness, the threshold value Thmin, the threshold value Thorax, and the filtering conditions, changed conditions are set and inputted by the user via the input unit 4 (S32, YES). Then, the operations in steps S14 to S30 are performed again based on the newly set and inputted conditions If the user does not change the pre-processing conditions, the process ends (S32, NO).

According to the mammographic imaging and display system of the above-described embodiment, a plurality of first tomographic images having the first slice thickness are generated based on a plurality of radiographic images, and a plurality of second tomographic images having the second slice thickness, which is greater than the first slice thickness, are generated based on the radiographic images. Then, the MinIP processing is applied to the first tomographic images to generate a MinIP image, and the MIP processing is applied to the second tomographic images to generate a MIP image. Then, combining processing is performed using the MinIP image and the MIP image to generate a composite image. This allows clearly showing calcified areas in the MinIP image based on the tomographic images having the relatively small slice thickness, and clearly showing the three-dimensional structure of a tumor mass area in the MIP image with high optical density contrast based on the tomographic images having the relatively large slice thickness. Therefore, both the calcified areas and the tumor mass area can be displayed with high resolution in the depth-direction, thereby improving the diagnosis accuracy.

Figure 8:
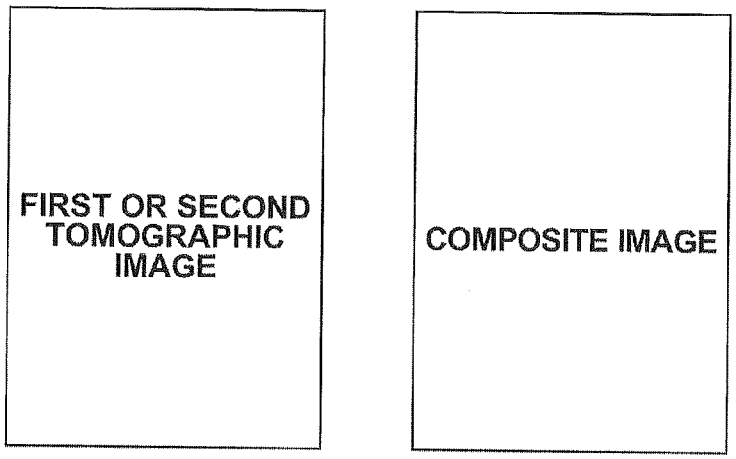
FIG. 8 is a diagram illustrating one example a display where a first or second tomographic image is displayed side by side with a composite image.

Although the composite image is displayed on the monitor 3 in the mammographic imaging and display system 1 of the above-described embodiment, the first tomographic image or the second tomographic image may be displayed side by side with the composite image, as shown in FIG. 8. Alternatively, any one of the radiographic images stored in the radiographic image storage unit 41 may be displayed side by side with the composite image.

Figure 9:
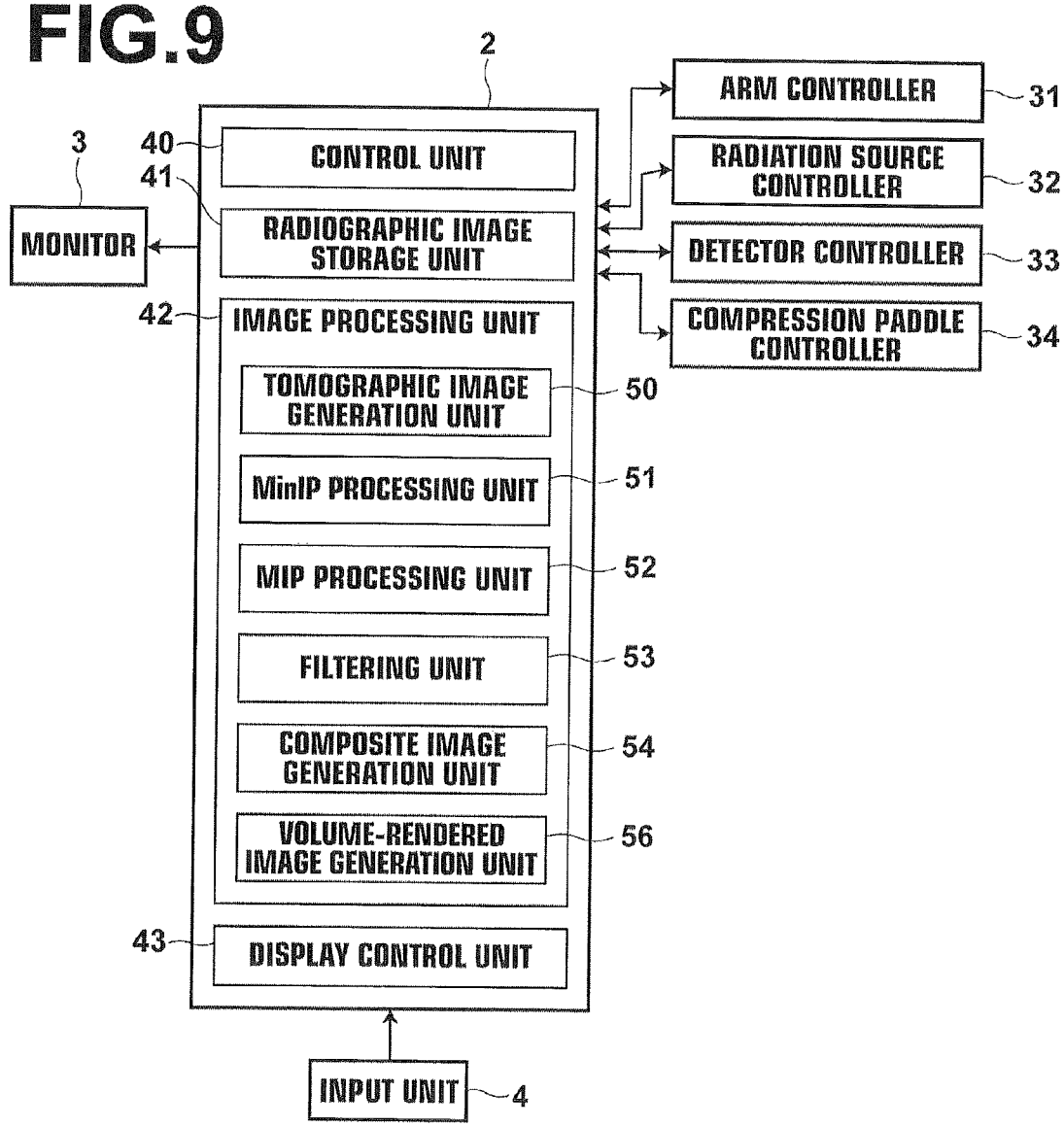
FIG. 9 is a diagram illustrating the schematic configuration of a mammographic imaging and display system employing another embodiment of the radiographic image generation device of the invention.

Further, as shown in FIG. 9, the mammographic imaging and display system 1 of the above-described embodiment may be provided with a volume-rendered image generation unit 56. The volume-rendered image generation unit 56 may generate a volume-rendered image using the tomographic images that are generated based on the radiographic images stored in the radiographic image storage unit 41.

Figure 10:
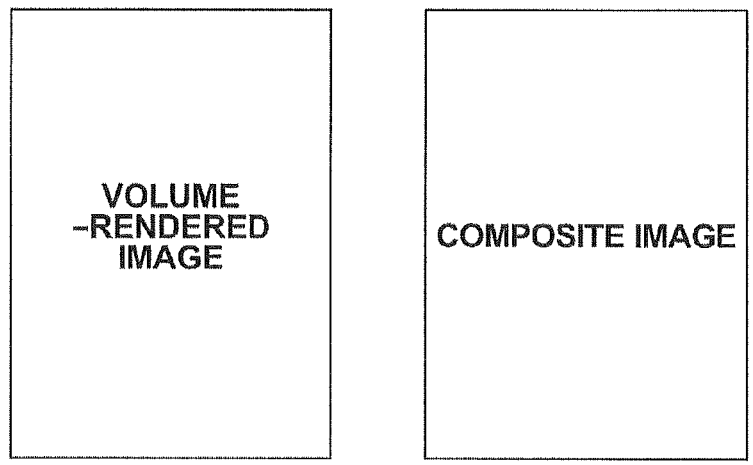
FIG. 10 is a diagram illustrating one example of a display where a volume-rendered image is displayed side by side with a composite image.

Then, as shown in FIG. 10, the display control unit 43 may display the volume-rendered image side by side with the composite image on the monitor 3. It should be noted that the tomographic images used to generate the volume-rendered image may be the first tomographic images having the first slice thickness or the second tomographic images having the second slice thickness. Alternatively, tomographic images having a slice thickness (such as 1 mm) different from the first slice thickness and the second slice thickness may be generated, and the volume-rendered image may be generated using the tomographic images.

Figure 11:
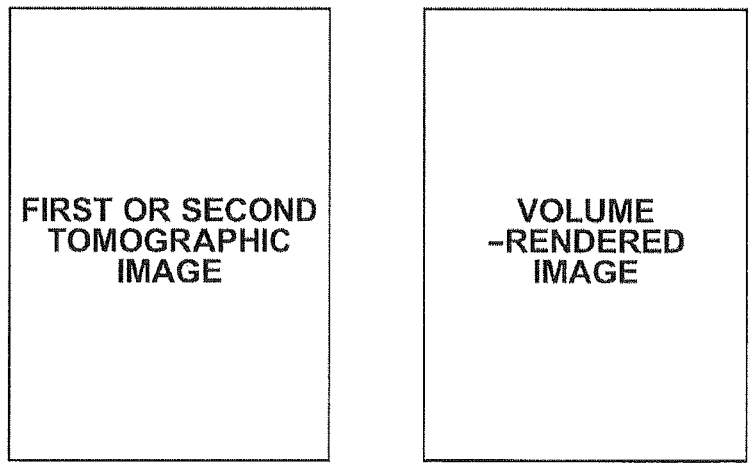
FIG. 11 is a diagram illustrating one example of a display where the first or second tomographic image is displayed side by side with the volume-rendered image.

In the case where the volume-rendered image is generated, as describe above, the first or second tomographic image may be displayed side by side with the volume-rendered image on the monitor 3, as shown in FIG. 11. Alternatively, any one of the radiographic images stored in the radiographic image storage unit 41 may be displayed side by side with the volume-rendered image.

Further, the user may select an image to be displayed from the radiographic images, the first tomographic images, the second tomographic images and the volume-rendered image via the input unit 4, and the display control unit 43 may display the image to be displayed selected by the user on the monitor 3. It should be noted that, at this time, a list of thumbnail images, for example, of the radiographic images, the first tomographic images, the second tomographic images and the volume-rendered image may be displayed on the monitor 3, and a selection screen for selection of the image to be displayed may be displayed on the monitor 3. It should be noted that, in this embodiment, the input unit 4 corresponds to an image selection receiving unit recited in the claims.

Figure 12:
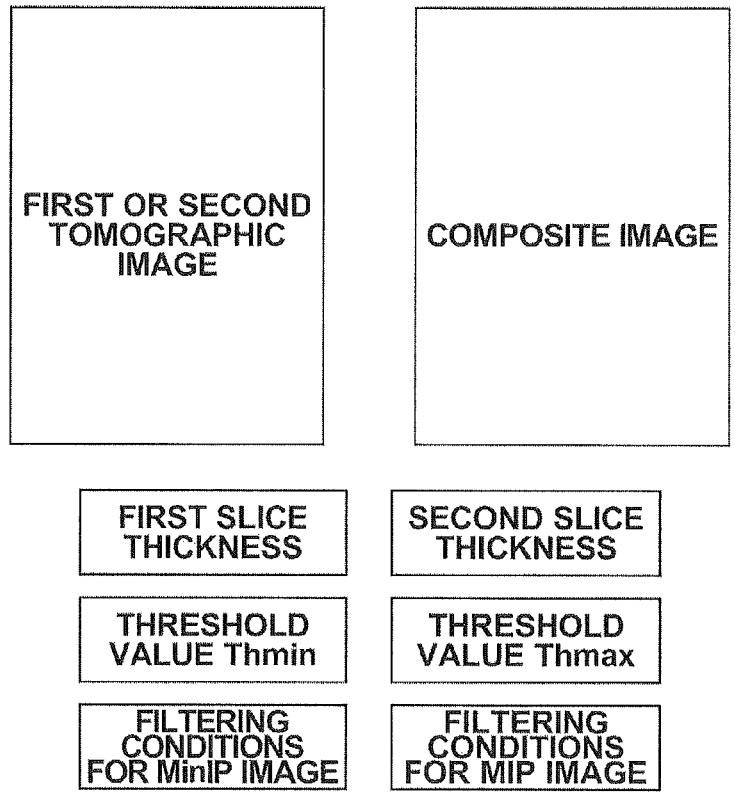
FIG. 12 is a diagram illustrating one example of a display where pre-processing conditions used to generate a composite image are displayed together with the composite image.

Further, in a case where the composite image is displayed on the monitor 3, pre-processing conditions, such as the first slice thickness of the first tomographic images and the second slice thickness of the second tomographic images used to generate the composite image, the threshold value Thmin used in the MinIP processing and the threshold value Thmax used in the MIP processing, the filtering conditions of the filtering applied to the MinIP image and the filtering applied to the MIP image, may be displayed together with the composite image on the monitor 3, as shown in FIG. 12.

Further, in a case where cinedisplay of composite images (where the composite images of different slice positions are sequentially displayed) is performed, if the first tomographic images forming the MIP image and the second tomographic images forming the MinIP image to be added to generate the composite images have different slice thicknesses, a difference between the slice position shown at portions formed by the MIP image and the slice position shown at portions formed by the MinIP image of each composite image is gradually increased, making the images difficult to observe.

Figure 13:
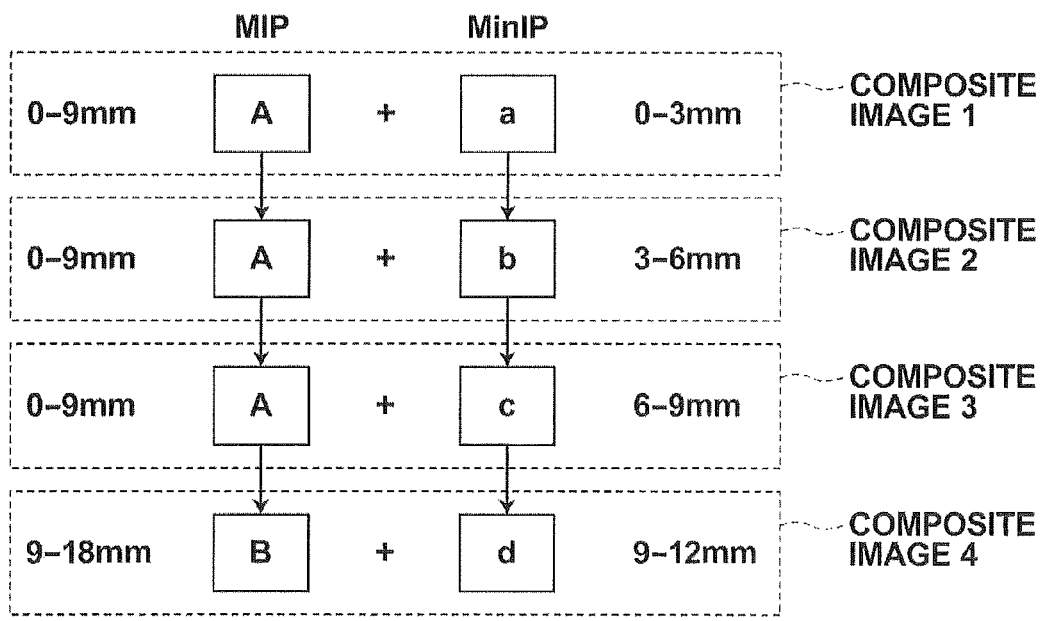
FIG. 13 is a diagram illustrating combinations of a MIP image and a MinIP image forming each composite image in a case where cinedisplay of composite images is performed.

Therefore, in a case where the first slice thickness of the first tomographic images forming the MinIP image is 3 mm and the second slice thickness of the second tomographic images forming the MIP image is 9 mm, which is three times the first slice thickness, and composite images 1 to 3 are generated, as shown in FIG. 13, each of first tomographic images a to c of different slice positions at 3-mm intervals is used in this order as the first tomographic image forming the MinIP image, and the second tomographic image A of the slice position of 0-9 mm is used three times as the second tomographic image forming the MIP image.

Then, when a composite image 4 is generated, a first tomographic image d of the slice position of 9-12 mm is used as the first tomographic image forming the MinIP image, and a second tomographic image B of the slice position of 9-19 mm is used as the second tomographic image forming the MIP image.

It should be noted that the example shown in FIG. 13 is of the case where the second slice thickness of the second tomographic images forming the MIP image is an integer multiple of the first slice thickness of the first tomographic images forming the MinIP image. On the other hand, in a case where the second slice thickness is not an integer multiple of the first slice thickness, such that the second slice thickness of the second tomographic images forming the MIP image is 5 mm and the first slice thickness of the first tomographic images forming the MinIP image is 2 mm, the cinedisplay of composite images without a feeling of strangeness can be achieved by using combinations of slice positions as shown in Table 1 below.

TABLE 1

| MinIP (mm) | 0-2 | 2-4 | 4-6 | 6-8 | 8-10 | 10-12 | 12-14 | 14-16 | 16-18 | 18-20 | 20-22 |
|---|---|---|---|---|---|---|---|---|---|---|---|
| MIP (mm) | 0-5 | 0-5 | 0-5 | 5-10 | 5-10 | 10-15 | 10-15 | 10-15 | 15-20 | 15-20 | 20-25 |

Although the radiographic image generation device and method of the invention are applied to the mammographic imaging and display system in the above-described embodiments, the subject is not limited to the breast in the invention. For example, the invention is also applicable to a radiographic imaging and display system provided with a tomosynthesis imaging function for so-called "general radiography" for imaging the chest, the head, or the like. In the case where the invention is applied to a radiographic imaging and display system for general radiography, information of the thickness of the subject may be obtained using an optical sensor, for example, or may be manually set and inputted by the user.

What is claimed is:

1. A radiographic image generation device comprising:
    a radiographic image obtaining unit for obtaining radiographic images for different imaging directions taken by applying radiation to a subject from the different imaging directions;
    a tomographic image generation unit for generating a plurality of first tomographic images having a first slice thickness based on the plurality of radiographic images obtained by the radiographic image obtaining unit and generating a plurality of second tomographic images having a second slice thickness that is greater than the first slice thickness based on the radiographic images;
    a MinIP processing unit for applying MinIP processing to the first tomographic images to generate a MinIP image;
    a MIP processing unit for applying MIP processing to the second tomographic images to generate a MIP image; and
    a composite image generation unit for performing combining processing using the MinIP image and the MIP image to generate a composite image.

2. The radiographic image generation device as claimed in claim 1, further comprising a high frequency extraction processing unit for applying high frequency extraction processing to extract high-frequency components to the MinIP image,
    wherein the composite image generation unit generates the composite image using the MinIP image subjected to the high-frequency extraction processing.

3. The radiographic image generation device as claimed in claim 1, further comprising a high frequency suppression processing unit for applying high-frequency suppression processing to suppress high-frequency components to the MIP image,
    wherein the composite image generation unit generates the composite image using the MIP image subjected to the high-frequency suppression processing.

4. The radiographic image generation device as claimed in claim 1, wherein the tomographic image generation unit sets the first slice thickness or the second slice thickness based on at least one of a range of the imaging directions of the radiographic images used to generate the first and second tomographic images, a type of a radiation source for applying the radiation, a thickness of the subject and patient information of the subject.

5. The radiographic image generation device as claimed in claim 1, further comprising a display control unit for displaying the composite image.

6. The radiographic image generation device as claimed in claim 5, wherein the display control unit displays the MinIP image and the MIP image in the composite image in different colors.

7. The radiographic image generation device as claimed in claim 5, wherein the display control unit displays the radiographic image, the first tomographic image or the second tomographic image side by side with the composite image.

8. The radiographic image generation device as claimed in claim 5, further comprising a volume-rendered image generation unit for generating a volume-rendered image using a plurality of tomographic images that are generated based on the radiographic images,
    wherein the display control unit displays the volume-rendered image side by side with the composite image.

9. The radiographic image generation device as claimed in claim 5, further comprising:
    a volume-rendered image generation unit for generating a volume-rendered image using a plurality of tomographic images that are generated based on the radiographic images; and
    an image selection receiving unit for receiving a selection of an image to be displayed from the radiographic images, the first tomographic images, the second tomographic images and the volume-rendered image,
    wherein the display control unit displays the image to be displayed received by the image selection receiving unit.

10. The radiographic image generation device as claimed in claim 2, wherein the high-frequency component extraction processing is high-pass filtering.

11. The radiographic image generation device as claimed in claim 3, wherein the high-frequency suppression processing is low-pass filtering.

12. A radiographic image generation method comprising:
    obtaining radiographic images for different imaging directions taken by applying radiation to a subject from the different imaging directions;
    generating a plurality of first tomographic images having a first slice thickness based on the obtained plurality of radiographic images and generating a plurality of second tomographic images having a second slice thickness that is greater than the first slice thickness based on the radiographic images;

applying MinIP processing to the first tomographic images to generate a MinIP image;

applying MIP processing to the second tomographic images to generate a MIP image; and performing combining processing using the MinIP image and the MIP image to generate a composite image.

* * * * *